United States Patent [19]

Takei et al.

[11] Patent Number: 4,464,532
[45] Date of Patent: Aug. 7, 1984

[54] INTERMEDIATES OF 7-ALKOXYCARBONYL-6,8-DIMETHYL-4-HYDROXYMETHYL-1-PHTHALAZONE

[75] Inventors: Yukio Takei, Abiko; Masao Yoshida; Rinzo Nishizawa, both of Tokyo, all of Japan

[73] Assignee: Nippon Kayaku Kabushiki Kaisha, Japan

[21] Appl. No.: 386,001

[22] Filed: Jun. 7, 1982

Related U.S. Application Data

[62] Division of Ser. No. 171,363, Jul. 23, 1980, Pat. No. 4,350,813.

[30] Foreign Application Priority Data

Jul. 31, 1979 [JP] Japan ................................. 54-96763
Jul. 31, 1979 [JP] Japan ................................. 54-96764

[51] Int. Cl.$^3$ ........................................... C07D 237/32
[52] U.S. Cl. .................................................... 544/237
[58] Field of Search ........................................ 544/237

[56] References Cited

U.S. PATENT DOCUMENTS 3,870,792 3/1975 Inoue ................................. 544/237
3,963,716 6/1976 Inoue ................................. 544/237
4,350,813 2/1984 Takei ................................. 544/237

FOREIGN PATENT DOCUMENTS 2711988 9/1977 Fed. Rep. of Germany ...... 544/237
100071 1/1974 Japan ................................. 544/237
9014484 2/1974 Japan ................................. 544/237
5019224 2/1980 Japan ................................. 544/237

OTHER PUBLICATIONS

Panomvana, D. L., "Prolonged Duration of Action of Dyphylline Through Prodrugs," *Dissertation Abst.* 40: #4232B.
Sinkula and Yalkowsky, "Rational for Design ... Prodrugs," *Pharm. Science* 64, pp. 181–210, (1975).

*Primary Examiner*—Donald G. Daus
*Assistant Examiner*—G. Hendricks
*Attorney, Agent, or Firm*—Henry C. Nields

[57] ABSTRACT

A novel process for producing 7-alkoxycarbonyl-6,8-dimethyl-4-hydroxymethyl-1-phthalazone, and its intermediates. 7-Alkoxycarbonyl-6,8-dimethyl-4-hydroxymethyl-1-phthalazone can be obtained by reacting substituted methylenetriphenylphosphorane with 3,5-dimethyl-4-alkoxycarbonylphthalic anhydride to obtain 6-alkoxycarbonyl-5,7-dimethyl-$\Delta^{3,\alpha}$-substituted methylenephthalide, reacting the latter with hydrazine to obtain a phthalazone derivative, hydrolyzing the latter, halogenating the hydrolyzate to obtain 7-alkoxycarbonyl-6,8-dimethyl-4-($\alpha$-halogeno-$\alpha$-substituted methyl)-1-phthalazone and then directly hydrolyzing and decarboxylating the latter or, when said 7-alkoxycarbonyl-6,8-dimethyl-4-($\alpha$-halogeno-$\alpha$-substituted methyl)-1-phthalazone is 7-alkoxycarbonyl-6,8-dimethyl-1-phthalazone-4-$\alpha$-halogenoacetic acid, reacting it with a carboxylic acid salt such as sodium acetate and simultaneously decarboxylating the acyloxylated compound and then hydrolyzing the decarboxylated product or firstly decarboxylating the 1-phthalazone-4-$\alpha$-halogenoacetic acid derivative, reacting the decarboxylated product with said carboxylic acid salt and then hydrolyzing the reaction product or when said 7-alkoxycarbonyl-6,8-dimethyl-4-($\alpha$-halogeno-$\alpha$-substituted methyl)-1-phthalazone is 7-alkoxycarbonyl-4-($\alpha$-carbamoyl-$\alpha$-halogenomethyl-6,8-dimethyl-1-phthalazone, reacting it with said carboxylic acid salt and then hydrolyzing and decarboxylating the acyloxylated compound simultaneously.

2 Claims, No Drawings

INTERMEDIATES OF 7-ALKOXYCARBONYL-6,8-DIMETHYL-4-HYDROXYMETHYL-1-PHTHALAZONE

This application is a division of application Ser. No. 171,363, filed July 23, 1980 now U.S. Pat. No. 4,350,813, issued Sept. 21, 1982.

BACKGROUND OF THE INVENTION

This invention relates to a novel process for producing 7-alkoxycarbonyl-6,8-dimethyl-4-hydroxymethyl-1-phthalazone, as well as to its intermediates.

7-Alkoxycarbonyl-6,8-dimethyl-4-hydroxymethyl-1-phthalazone (hereinafter referred to as 4-hydroxymethyl-1-phthalazone) represented by the following formula:

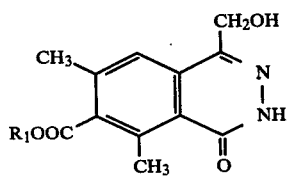

wherein $R_1$ is a lower alkyl, is a compound originally produced by Shimamoto, Ishikawa et al. through a structure-activity relationship study of a series of compounds having phthalazone skeleton. Having a very strong inhibitory action on the coagulation of blood platelets and an inhibitory action on phosphodiesterase, this compound is expected as an effective therapeutic medicine for cerebral hemorrhage, atherosclerosis and cerebral apolexy (U.S. Pat. No. 3,963,716; Austrian Pat. No. 7,408,744).

The process mentioned in the above-mentioned patent has a fault that mass production of the objective compound is difficult because the starting compound itself is difficult to synthesize.

For example, in the process for synthesizing 5,7-dimethyl-6-ethoxycarbonyl-3-hydroxy-3-methylphthalide (B) by reacting 3,5-dimethyl-4-ethoxycarbonylphthalic anhydride (A) with dimethylcadmium as shown in the following scheme:

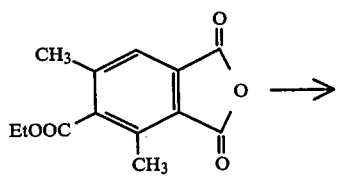

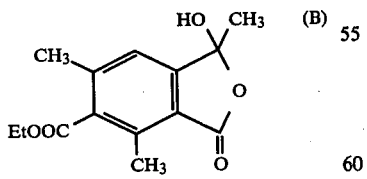

the cadmium is a dangerous heavy metal and the reaction requires to use a large quantity of ether under an anhydrous condition, so that the process is undesirable as an industrial production process.

In the process for synthesizing the phthalide derivative (B) by reacting the above-mentioned phthalic anhydride derivative (A) with malonic acid (Japanese Patent Kokai (Laid-Open)) No. 84,563/1975) a position isomer (C) represented by the following formula:

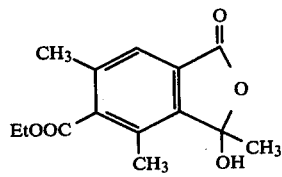

is formed as a by-product.

The present inventors found out a process suitable for mass production and having no faults mentioned above.

According to the process of this invention, the objective compound can be obtained from an inexpensive starting material in a high yield.

DETAILED DESCRIPTION OF THE INVENTION

This invention will be illustrated below in detail.

According to the process of this invention, 4-hydroxymethyl-1-phthalazone represented by formula (VIII) can be synthesized in the following manner.

Thus, 4-hydroxymethyl-1-phthalazone represented by the following formula (VIII):

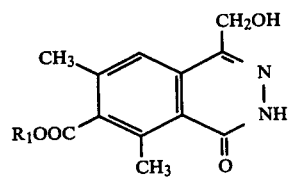

wherein $R_1$ is a lower alkyl, is produced by:

(A) reacting 3,5-dimethyl-4-alkoxycarbonylphthalic anhydride represented by the following formula:

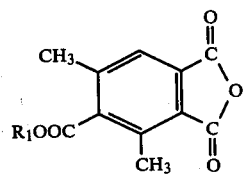

wherein $R_1$ is as defined above, with a compound represented by the following formula:

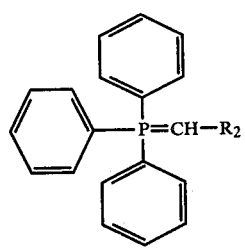

wherein $R_2$ is —CN or —COOEs is (Es is an ester residue) to obtain 6-alkoxycarbonyl-5,7-dimethyl-$\Delta^{3,\alpha}$-substituted methylenephthalide (hereinafter referred to as methylenephthalide) represented by the following formula:

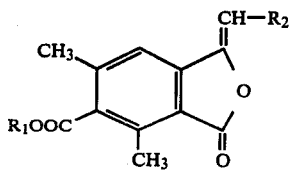

(III)

wherein $R_1$ and $R_2$ are as defined above, followed by (B) reacting the methylenephthalide compound of formula (III) with hydrazine to obtain a compound represented by the following formula:

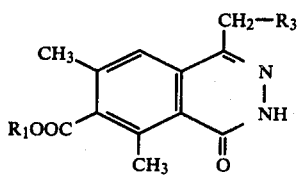

(IV)

wherein $R_1$ is as defined above and $R_3$ is —CN or —CONHNH$_2$, (C) hydrolyzing the compound of formula (IV) to obtain 7-alkoxycarbonyl-6,8-dimethyl-4-substituted methyl-1-phthalazone (hereinafter referred to as 4-substituted methyl-1-phthalazone) represented by the following formula:

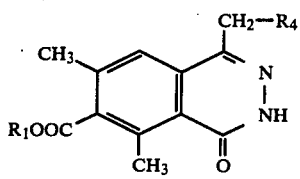

(V)

wherein $R_1$ is as defined above and $R_4$ is —CONH$_2$ or —COOH, (D) halogenating the compound of formula (V) to obtain 7-alkoxycarbonyl-6,8-dimethyl-4-(α-halogeno-α-substituted methyl)-1-phthalazone [hereinafter referred to as 4-(α-halogeno-α-substituted methyl)-1-phthalazone] represented by the following formula:

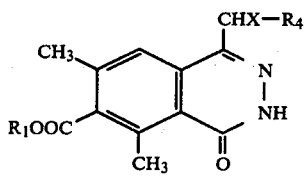

(VI)

wherein $R_1$ and $R_4$ are as defined above and X is halogen atom, and then (E) hydrolyzing and decarboxylating the compound of formula (VI) by either of the following methods (a) and (b):

(a) directly hydrolyzing and decarboxylating the compound of formula (VI), (b) when $R_4$ is —COOH in the compound of formula (VI), reacting the compound of formula (VI) with a carboxylic acid salt represented by the following formula:

($R_5$COO)$_n$M  (VII)

wherein $R_5$ is a hydrogen atom, an alkyl, aryl or aralkyl, M is alkali metal or alkaline earth metal, and n is 1 when M is alkali metal and 2 when M is alkaline earth metal, and simultaneously decarboxylating the acyloxylated compound and then hydrolyzing the decarboxylated compound, or firstly decarboxylating the compound of formula (VI), reacting the product with the carboxylic acid salt of formula (VII) and then hydrolyzing the reaction product.

(c) when $R_4$ in formula (VI) is —COHN$_2$, reacting the compound of formula (VI) with the carboxylic acid salt of formula (VII), and then hydrolyzing and decarboxylating the acyloxylated compound simultaneously.

The characteristic features of this invention consists in that the methylenephthalide represented by formula (III) can be produced in a very high yield by reacting 3,5-dimethyl-4-alkoxycarbonylphthalic anhydride represented by formula (I) with the compound represented by formula (II) without forming the unnecessary position isomer represented by the following formula:

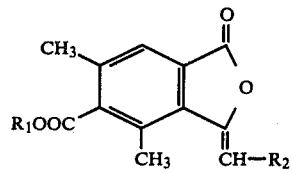

at all and that a series of reactions starting from the methylenephthalide of formula (III) are quite conventional in reaction conditions and easy in operation, the starting material is inexpensive and the overall yield is very high.

Most of the intermediates obtained in a series of steps of this invention are novel compounds.

For example, the compound of formula (IV) and the compound of formula (V) are both novel, and they can be represented generally by the following formula:

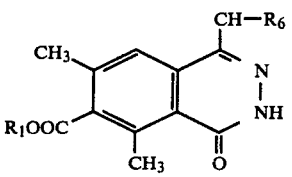

wherein $R_1$ is as defined above and $R_6$ is —CH, —CONHNH$_2$, —CONH$_2$ or —COOH. The compounds of formula (III) and formula (VI) are also novel.

In this invention, the reaction of step (A) between 3,5-dimethyl-4-alkoxycarbonylphthalic anhydride of formula (I) and the compound of formula (II) is usually carried out in the presence of a solvent and preferably organic solvent, usually at a temperature ranging from 0° C. to the boiling point of the solvent and preferably from 0° C. to about 50° C. The reaction can usually be completed in a reaction time of 2-4 hours. Though the solvent used is not particularly limited to long as it is inert to the reaction, examples of the preferable solvent include aromatic hydrocarbons such as benzene, toluene and xylene, halogenated hydrocarbons such as methylene chloride, chloroform and carbon tetrachloride, and ethers such as ethyl ether, isopropyl ether, tetrahydrofuran and dioxane.

The reaction is carried out by using the compound of formula (II) in an amount of 0.5 to 2.0 moles per 1 mole of 3,5-dimethyl-4-alkoxycarbonylphthalic anhydride of formula (I). Preferably, the inexpensive compound of formula (II) is used in an amount of 1.0-1.3 moles per 1 mole of the latter. The methylenephthalide of formula (III) obtained by this reaction is a 5-7:1 mixture of the geometric isomers (III′) and (III″) shown below:

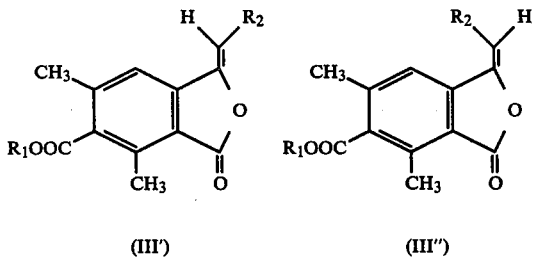

Since these geometric isomers give the same compound of formula (IV) when reacted with hydrazine in the subsequent step, it is unnecessary to separate them from each other. Further, the triphenylphosphine oxide formed in this reaction effects no harmful influence in the subsequent reaction. Therefore, the liquid reaction mixture itself or the residue obtained by distilling off the solvent therefrom can be used as a crude product in the subsequent reaction. When isolation of the product (III) is necessary, column chromatography by the use of silica gel is most suitable. It is also possible to isolate the product (III′) either directly from the reaction mixture or by recrystallization of the crude product because, among the geometric isomers, the isomer (III′) has a lower solubility in aromatic hydrocarbon solvents then the other isomer (III″).

Many of the 3,5-dimethyl-4-alkoxycarbonylphthalic anhydrides represented by formula (I) are known compounds. For example, some of them can be obtained easily by condensing an alkyl ester of isodehydroacetic acid with a diester of acetylenedicarboxylic acid to produce a phthalic diester derivative, saponifying the latter and then treating the saponified product with acetic anhydride.

The lower alkyl of $R_1$ in formula (I) are, for example, methyl, ethyl, propyl, butyl, pentyl and hexyl, which are not limited to a straight chain alkyl but may be branched if branching is possible. Halogen atoms of X in formula (VI) are chlorine, bromine, iodine, and fluorine.

$R_2$ of formula (II) is —CN of —COOEs (Es is ester residue) and examples of —COOEs include lower alkoxy($C_1$-$C_6$)-carbonyls such as methoxycarbonyl, ethoxycarbonyl, propoxycarbonyl and butoxycarbonyl; aralkoxycarbonyls such as benzyloxycarbonyl, phenylethyloxycarbonyl, chlorophenylpropoxycarbonyl; aryloxycarbonyls such as phenoxycarbonyl and substituted phenoxycarbonyls. Usually, the compound of formula (II) can be obtained by reacting triphenylphosphine with bromacetic ester or bromacetonitrile and most of them are disclosed compounds.

In the subsequent step (B), the reaction of the methylenephthalide of formula (III) and hydrazine can usually be carried out in the presence of a solvent at a temperature ranging from room temperature to the boiling point of the solvent, preferably at a temperature of 80° C. to about 130° C. Though the hydrazine can be used in any state and in any content, it is convenient to use a 80% aqueous solution of hydrazine hydrate. It can be used in an amount of about 2-10 moles, preferably about 3-6 moles, per 1 mole of the methylenephthalide of formula (III). The solvent is not particularly limited. Those miscible with water are preferable. Examples of the preferable solvent include alcohols such as methanol, ethanol, propanol and butanol; ethers such as tetrahydrofuran and dioxane; dimethyl sulfoxide; dimethylformamide; and the mixtures of these solvent with water.

When, for example, 80% aqueous solution of hydrazine hydrate is used as a sort of hydrazine and n-propanol as a solvent, the isolation of the compound of formula (IV) from the reaction mixture can easily be carried out by cooling the reaction mixture after the reaction and then collecting the resulting crystalline precipitates by filtration. When 80% aqueous solution of hydrazine hydrate is reacted by using ethanol as a solvent, the isolation can easily be performed by concentrating the liquid reaction mixture under reduced pressure after the reaction and recrystallizing the residue from ethanol.

Next, the subsequent step (C) will be illustrated.

In the hydrolysis of step (C) for obtaining 4-substituted methyl-1-phthalazone of formula (V) from the compound of formula (IV), either of acid and base may be used as the hydrolyzing reagent. As said acid, mineral acids such as hydrochloric acid, hydrobromic acid, sulfuric acid and nitric acid are preferable and organic sulfonic acids such as benzenesulfonic acid, p-toluenesulfonic acid and methanesulfonic acid can also be used. As said base, alkali hydroxides such as sodium hydroxide, potassium hydroxide, alkali carbonates such as sodium carbonate, potassium carbonate, potassium hydrogen carbonate and sodium hydrogen carbonate and alkaline earth metal hydroxides such as calcium hydroxide are used preferably.

Said hydrolyzing agent is used in an amount of 1-20 equivalents and usually 2-5 equivalents to the compound of formula (IV).

The solvent for the reaction is not particularly limited. Water and solvents miscible with water are preferable, of which examples include alcohols such as methanol, ethanol and propanol; ketones such as acetone and methylethylketone; ethers such as cyclic ethers, for example, tetrahydrofuran and dioxane; and mixtures of water and these water-soluble solvents.

The reaction can be carried out at a temperature ranging from room temperature to the boiling point of the solvent, preferably about 80° C. to 110° C.

When the hydrolysis is carried out with hydrochloric acid by using water as a solvent, the isolation of 4-substituted methyl-1-phthalazone of formula (V) from the reaction mixture can be practised by collecting the deposited crystals after the reaction by filtration to obtain a crude product and, if necessary, recrystallizing it from, for example, a solvent mixture of water and acetone.

Next, step (D) i.e. the halogenation of the 4-substituted methyl-1-phthalazone of formula (V) is usually carried out in a solvent with a halogenating agent. Said halogenating agent is not particularly limited. Preferred halogenating agents are, for example, chlorine, bromine, N-chlorosuccinimide, N-bromosuccinimide, N-iodosuccinimide, sulfuryl chloride, cupric chloride, cupric bromide, phosphorus trichloride, phosphorus tribromide and phosphorus pentachloride. The halogenating agent is used in an amount of 0.5-2.0 moles, preferably 1.0–1.3 moles, per 1 mole of the 4-substituted methyl-1-phthalazone of formula (V).

The solvent used in the reaction is not particularly limited so long as it is inert to the reaction, and any appropriate solvent may be selected in accordance with the kind of the halogenating agent used. Generally, halogenated hydrocarbons such as methylene chloride, chloroform and carbon tetrachloride; ethers such as ethyl ether, tetrahydrofuran, dioxane; organic acids such as formic acid, acetic acid and propionic acid; dimethylformamide; and water are used.

The reaction can be preferably practised at a temperature ranging from room temperature (about 20° C.) to the boiling point of the solvent, and is usually completed within 12 hours.

When bromine is used as the halogenating agent, acetic acid as the solvent and $R_4$ in formula (VI) is —COOH, the isolation of 4-(α-halogeno-α-substituted methyl)-1-phthalazone of formula (VI) from the reaction mixture can be performed by distilling off the solvent after the reaction, adding water to the residue, collecting the resulting crystals by filtration and, if necessary, recrystallizing them with a mixture of acetone and hexane.

When $R_4$ in formula (VI) is —CONH$_2$, bromine is used as the halogenating agent and acetic acid as the solvent, the isolation can be carried out by distilling off the solvent after the reaction, dissolving the residue into chloroform, washing the chloroform solution with cold water, drying it over anhydrous sodium sulfate, filtering off the drying agent, concentrating the filtrate under reduced pressure and recrystallizing the residue from chloroform.

Next, step (E) for converting the 4-(α-halogeno-α-substituted methyl)-1-phthalazone of formula (VI) to the 4-hydroxymethyl-1-phthalazone of formula (VIII) will be illustrated.

Firstly (a) of step (E) i.e. the direct hydrolysis and decarboxylation of the compound of formula (VI) will be illustrated.

The hydrolysis of the compound of formula (VI) can be carried out in the same manner as in the compound of formula (IV) of step (C). When an acid is used in this hydrolysis as a hydrolyzing agent, the hydrolysis and the decarboxylation can be effected simultaneously. When the hydrolysis is carried out with a base, there is usually formed in the course of the reaction a salt of 7-alkoxycarbonyl-6,8-dimethyl-1-phthalazone-4-α-hydroxyacetic acid represented by the following formula:

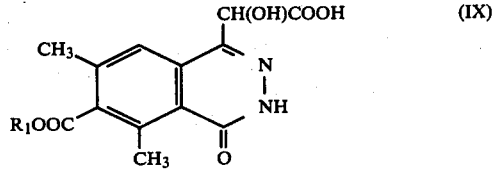
(IX)

wherein $R_1$ is as defined above. In this case, the compound of formula (IX) may be decarboxylated either after the isolation of said compound or without isolation. The decarboxylation of the compound of formula (IX) can be effected in either neutral or acidic condition. It is generally preferable to carry out the decarboxylation under an acidic condition. Various acids can be used for the acidic condition. For example, formic acid, acetic acid, propionic acid, benzenesulfonic acid, toluenesulfonic acid, phenylacetic acid are preferable as organic acid and sulfuric acid, hydrochloric acid and nitric acid are preferable as inorganic acid.

The solvent may be either used or not. When a solvent is used, it is not particularly limited so long as it is inert to the reaction. Water alone is also usable. Preferred solvents include aromatic hydrocarbons such as benzene, toluene and xylene; alcohols such as methanol, ethanol and propanol; organic acids such as formic acid, acetic acid and propionic acid; ketones such as acetone and methyl ethyl ketone; ethers such as cyclic ether, for example, dioxane and tetrahydrofuran; and their mixtures with water.

In the hydrolysis of the compound of formula (VI), the acid is used as a catalyst, so that its amount is not particularly limited and usually its 0.01–1.0 equivalent is employed. The reaction temperature and reaction time are selected from wide ranges in accordance with the kind of acid or base and the solvent used, when a solvent is used the reaction is preferably carried out at a temperature ranging from room temperature to the boiling point of the solvent. The reaction is usually completed in 1–10 hours.

When a solvent mixture comprising water and an organic solvent is used in the reaction for example, the isolation of the 4-hydroxymethyl-1-phthalazone of formula (VIII) from the reaction mixture is carried out by distilling off the organic solvent, adding water to the residual reaction mixture, adjusting its pH to about 4 with a base or an acid and collecting the depositing crystals by filtration.

Next, (b) of step (E) will be illustrated.

When $R_4$ of the compound of formula (VI) is —COOH, the hydrolysis and the decarboxylation can be practised by method (b) more preferably, though it can also be practised by method (a).

According to the first method of (b), decarboxylation also takes place simultaneously when the carboxylic acid salt of formula (VII) is reacted with 4-(α-halogeno-α-substituted methyl)-1-phthalazone of formula (VI), so that a subsequent hydrolysis can give the objective compound.

The following intermediate is formed by the reaction of the carboxylic acid salt of formula (VII) with the compound of formula (VI) and simultaneous decarboxylation.

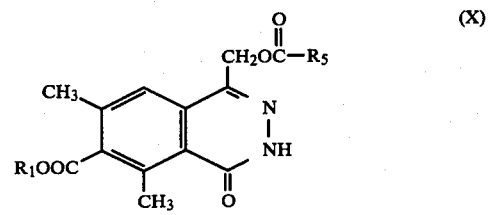
(X)

wherein $R_1$ and $R_5$ are as defined above. Either the resultant reaction mixture or the intermediate isolated from said mixture can be used in the subsequent hydrolysis process.

The reaction between the compound of formula (VI) and the carboxylic acid salt of formula (VII) is usually carried out in the presence of a solvent. Sovents inert to this reaction can be used for this purpose, of which examples include fatty acids such as formic acid, acetic acid and propionic acid; ketones such as acetone and methyl ethyl ketone; ethers such as cyclic ethers, for example, tetrahydrofuran and dioxane; aromatic hydrocarbons such as benzene, toluene and xylene; dimethyl sulfoxide and dimethylformamide.

If, in this reaction, a fatty acid salt is used as the carboxylic acid salt of formula (VII) and a fatty acid is used as the solvent, it is preferable to use, as the solvent, the fatty acid corresponding to said carboxylic acid salt of formula (VII). For example, when the carboxylic acid salt of formula (VII) is sodium acetate, the solvent is preferably acetic acid.

The carboxylic acid salt of formula (VII) is used usually in an amount of 1–10 moles, preferably 1.5–5 moles, per 1 mole of the compound of formula (VI).

The reaction temperature and the reaction time are selected from wide ranges in accordance with the kinds of starting material and solvent. It is usually preferable to carry out the reaction at temperature from room temperature (about 20° C.) to the boiling point of the solvent used in the reaction. The reaction is usually completed in about 10 hours.

The examples of $R_5$ in the formula (VII) are hydrogen atom, an alkyl such as methyl, ethyl, propyl, butyl, pentyl, hexyl and heptadecyl; an aryl such as phenyl and naphthalyl and an aralkyl such as benzyl, phenylethyl and naphthylmethyl. An alkyl is not only straight chain but also may be branched if it may be branched. Further, these alkyl, phenyl, naphthyl may be substituted with other substituents other than hydrogen unless they have an undesirable effect on the reaction.

The examples of M in the formula (VII) are alkali metals such as sodium and potassium and alkaline earth metals such as calcium and magnesium, provided that n is 1 when M is an alkali metal and n is 2 when M is an alkaline earth metal. It is sometimes preferable to carry out this reaction in the presence of a catalyst. Particularly when the above-mentioned ketones, cyclic ethers or aromatic hydrocarbons are used as the solvent, the reaction is preferably conducted in the presence of the catalyst such as a crown ether typified by 18-crown-6, among which 18-crown-6 itself is particularly preferable. It can be added in an amount of about 0.1–10% (by weight), preferably about 1–5% based on the carboxylic acid salt of formula (VII).

The subsequent step of hydrolysis can be practised in the same way as in the hydrolysis in the first step of (C).

Next, the second method of (b) wherein decarboxylation is carried out at the beginning which is followed by the reaction with the carboxylic acid salt of formula (VII) and hydrolysis will be illustrated.

The first decarboxylation from the compound of formula (VI) can be carried out by a mere heating in the presence or absence of a solvent. It is preferably carried out in a solvent inert to the reaction. Examples of the solvents are organic acids such as formic acid, acetic acid and propionic acid and aromatic hydrocarbons such as benzene, toluene, and xylene.

The reaction can be carried out at the temperature from 50° C. to 250° C. in general, the reaction is most preferably carried out at the temperature from 80° C. to 120° C. in the presence of the solvent. The reaction time varies depending on the temperature. The reaction usually can be completed in several minutes to about 3 hours.

By the decarboxylation, there is formed a compound represented by the following formula:

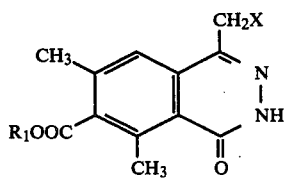

wherein $R_1$ and X are as defined above, as an intermediate. This intermediate may be isolated before reacting it with the carboxylic acid salt of formula (VII) in the subsequent step but the reaction mixture including said intermediate can also be used in the subsequent step. The reaction of said intermediate and the carboxylic acid salt of formula (VII) can be effected in the same way as in the above-mentioned reaction between the compound of formula (VI) and the carboxylic acid salt of formula (VII).

By the reaction between the compound of formula (XI) and the carboxylic acid salt of formula (VII), the above-mentioned compound of formula (X) is formed as an intermediate. Hydrolysis of this compound of formula (X) can be effected in the same manner as above.

Lastly, (c) of step (E) will be illustrated. When $R_4$ in formula (VI) is $-CONH_2$, the reaction of the compound of formula (VI) and the carboxylic acid salt of formula (VII) can be performed in the same way as the reaction in the method (b) of step (E).

Simultaneous hydrolysis and decarboxylation of the acyloxylated compound can be carried out in the same way as the hydrolysis used an acid in step (C).

The objective compound thus obtained i.e. 4-hydroxymethyl-1-phthalazone of formula (VIII) can be isolated by removing the organic solvent by a method such as distillation, followed by adjusting pH to about 4 and collecting the depositing crystals by filtration, when a solvent mixture comprising water and an organic solvent is used as the solvent.

This invention will be specified by the following Examples, which are presented in no limitative way.

EXAMPLE 1

Benzene (10 ml) is added to a mixture of 2.50 g of 3,5-dimethyl-4-ethoxycarbonylphthalic anhydride and 4.35 g of methoxycarbonylmethylenetriphenylphosphorane, and the mixture is reacted at room temperature with stirring for 4 hours. After the reaction, the solvent is distilled off under reduced pressure to give a crude product. It is subjected to a column chromatography using 150 g of silica gel and a benzene-ethyl acetate mixture as the developing solvent, whereby the two products having a relation of geometric isomer to each other can be isolated:

methyl (Z)-5,7-dimethyl-6-ethoxycarbonylphthalide-$\Delta^{3,\alpha}$-methylenecarboxylate; 2.20 g (yield 72.3%); m.p. 122.0°–122.5° C.

methyl (E)-5,7-dimethyl-6-ethoxycarbonylphthalide-$\Delta^{3,\alpha}$-methylenecarboxylate; 0.34 g (yield 11.2%); m.p. 134°–136° C.

EXAMPLE 2

Benzene (30 ml) is added to a mixture of 3.72 g of 3,5-dimethyl-4-ethoxycarbonylphthalic anhydride and 6.20 g of ethoxycarbonylmethylenetriphenylphosphorane and the mixture is reacted at room temperature for 3 hours with stirring. After the reaction the deposited crystals are collected by filtration, and there is obtained 1.23 g (yield 25.8%) of ethyl (Z)-5,7-dimethyl-6-ethoxycarbonylphthalide-$\Delta^{3,\alpha}$-methylenecarboxylate; m.p. 114°–114.5° C.

The filtrate is concentrated, and the residue is subjected to silica gel chromatography in the same manner as in Example 1, and there is additionally obtained 2.11 g (yield 44.2%) of ethyl (Z)-5,7-dimethyl-6-ethoxycarbonylphthalide-$\Delta^{3,\alpha}$-methylenecarboxylate. By this chromatography, there is simultaneously obtained 0.80 g (yield 16.8%) of ethyl (E)-5,7-dimethyl-6-ethoxycarbonylphthalide-$\Delta^{3,\alpha}$-methylenecarboxylate; m.p. 105°–108° C.

EXAMPLE 3

Benzene (3 ml) is added to a mixture of 0.50 g of 3,5-dimethyl-4-methoxycarbonylphthalic anhydride and 0.97 g of ethoxycarbonylmethylenetriphenylphosphorane, the mixture is reacted at room temperature for 3 hours with stirring and the deposited crystals are collected by filtration, whereby 0.26 g (yield 40.1%) of ethyl (Z)-5,7-dimethyl-6-methoxycarbonylphthalide-$\Delta^{3,\alpha}$-methylenecarboxylate is obtained; m.p. 127°–128.5° C.

EXAMPLE 4

Ethyl (Z)-5,7-dimethyl-6-ethoxycarbonylphthalide-$\Delta^{3,\alpha}$-methylenecarboxylate (2.48 g) is added into a mixture of 50 ml of n-propanol and 4.70 g of 80% aqueous solution of hydrazine hydrate, and then the mixture is heated under reflux at 110° C. for 10 hours. The reaction mixture is cooled and the deposited crystals are collected by filtration to obtain 2.25 g (yield 90.7%) of 6,8-dimethyl-7-ethoxycarbonyl-1-phthalazone-4-acetic acid hydrazide.

m.p. 243°–245° C. (decomposition with foaming)

IR spectrum: $\nu_{max}^{KBr}$ (cm$^{-1}$)=3320, 3180, 1724, 1655, 1604, 1526, 1280

NMR spectrum (DMSO-d$_6$): $\delta$=1.35 (t, 3H, J=7 Hz; OCH$_2$CH$_3$), 2.39, 2.78 (s, s, 3H, 3H; phenyl—CH$_3$), 3.72 (s, 2H; CH$_2$), 4.40 (q, 2H, J=7 Hz; OCH$_2$CH$_3$), 3.5–4.7 (broad, 2H; NH$_2$), 7.60 (s, 1H; phenyl—H), 9.25 (s, 1H; NHNH$_2$), 12.36 (s, 1H; NH—N=)

EXAMPLE 5

Ethyl (E,Z)-5,7-dimethyl-6-ethoxycarbonylphthalide-$\Delta^{3,\alpha}$-methylenecarboxylate [the above-mentioned geometric isomer mixture, (III′):(III″)=9:4] (0.33 g) is dissolved into 7 ml of n-propanol, to which is added 0.63 g of 80% aqueous solution of hydrazine hydrate. The reaction and the after-treatment are carried out in the same manner as in Example 4, whereby 0.31 g (yield 93.6%) of 6,8-dimethyl-7-ethoxycarbonyl-1-phthalazone-4-acetic acid hydrazide is obtained.

This product perfectly coincides with the product of Example 4 in m.p., IR and NMR spectra.

EXAMPLE 6

Ethyl (Z)-5,7-dimethyl-6-methoxycarbonylphthalide-$\Delta^{3,\alpha}$-methylenecarboxylate (0.20 g) is dissolved into 4 ml of n-propanol, to which is added 0.41 g of 80% aqueous solution of hydrazine hydrate. Thereafter, the reaction and the after-treatment are carried out in the same manner as in Example 4. Thus 0.14 g (yield 68.2%) of 6,8-dimethyl-7-methoxycarbonyl-1-phthalazone-4-acetic acid hydrazide is obtained.

m.p. 257.5°–259.0° C. (decomposition with foaming)

IR spectrum: $\theta_{max}^{KBr}$ (cm$^{-1}$)=3300, 3170, 3040, 2940, 1725, 1650, 1603, 1532, 1435, 1285

NMR spectrum (DMSO-d$_6$): $\delta$=2.38, 2.76 (s, s, 3H, 3H; phenyl—CH$_3$), 3.72 (s, 2H; CH$_2$), 3.94 (s, 3H; CH$_3$O), 3.6–4.7 (broad, 2H; NH$_2$), 7.64 (s, 1H; phenyl—H), 9.26 (s, 1H; NHNH$_2$), 12.38 (s, 1H; NH—N=)

EXAMPLE 7

3,5-Dimethyl-4-ethoxycarbonylphthalic anhydride (25.0 g) and 43.5 g of methoxycarbonylmethylenetriphenylphosphorane are added to 100 ml of benzene and stirred at 20°–25° C. for 4 hours. After the reaction, the reaction mixture is concentrated under reduced pressure, the residue is added into 800 ml of n-propanol and 64.0 g of 80% aqueous solution of hydrazine hydrate is added, and the mixture is heated under reflux for 10 hours. The reaction mixture is cooled and the depositing crystals are collected by filtration. Thus, 27.2 g (yield 85.4%) of 6,8-dimethyl-7-ethoxycarbonyl-1-phthalazone-4-acetic acid hydrazide is obtained. This product perfectly coincides with the product of Example 4 in m.p., IR and NMR spectra.

EXAMPLE 8

6,8-Dimethyl-7-ethoxycarbonyl-1-phthalazone-4-acetic acid hydrazide (12.00 g) is added to 380 ml of 2N hydrochloric acid and heated under reflux for 5 hours. The reaction mixture is cooled and the depositing crystals are collected by filtration, washed with water and dried. Thus, 10.2 g (yield 89.0%) of 6,8-dimethyl-7-ethoxycarbonyl-1-phthalazone-4-acetic acid is obtained.

m.p. 162.5°–163.5° C. (decomposition with foaming)

IR spectrum: $\nu_{max}^{KBr}$ (cm$^{-1}$)=3240, 2300–3000 (broad), 1730, 1700 (shoulder), 1640, 1602, 1280

NMR spectrum (DMSO-d$_6$): $\delta$=1.37 (t, 3H, J=7 Hz; OCH$_2$CH$_3$), 2.42, 2.82 (s, s, 3H, 3H; phenyl—CH$_3$), 3.94 (s, 2H; CH$_2$), 4.43 (q, 2H, J=7 Hz; OCH$_2$CH$_3$), 2–6 (broad, 1H; COOH), 7.61 (s, 1H; phenyl—H), 12.45 (s, 1H; NH)

EXAMPLE 9

6,8-Dimethyl-7-ethoxycarbonyl-1-phthalazone-4-acetic acid anhydride (2.00 g) is added to 50 ml of 3N hydrochloric acid and heated under reflux for 2 hours, after which it is treated in the same manner as in Example 8. Thus, 1.80 g (yield 94.4%) of 6,8-dimethyl-7-methoxycarbonyl-1-phthalazone-4-acetic acid is obtained.

m.p. 203°–205° C. (decomposition with foaming)

IR spectrum: $\nu_{max}^{KBr}$ (cm$^{-1}$)=3300, 3160, 3035, 2300–3000 (broad), 1733, 1697, 1663, 1603, 1438, 1290, 1250, 1175, 1145

NMR spectrum (DMSO-d$_6$): $\delta$=2.40, 2.78 (s, s, 3H, 3H; phenyl—CH$_3$), 3.96 (s, 5H; CH$_2$, CH$_3$O), 5–10 (broad, 1H; COOH), 7.61 (s, 1H; phenyl—H), 2.45 (s, 1H; NH)

EXAMPLE 10

6,8-Dimethyl-7-ethoxycarbonyl-1-phthalazone-4-acetic acid (0.40 g) is dissolved into 10 ml of glacial acetic acid, 0.24 g of bromine is added thereto, and the mixture is reacted at room temperature for 3 hours with stirring. The acetic acid is distilled off under reduced pressure, water is added to the residue, the deposited crystals are collected by filtration and the crystals recrystallized from acetone-n-hexane mixture. Thus, 0.47 g (yield 92.9%) of 6,8-dimethyl-7-ethoxycarbonyl-1-phthalazone-4-$\alpha$-bromoacetic acid is obtained. m.p. 202.5°–204° C.

example, tetrahydrofuran and dioxane; aromatic hydrocarbons such as benzene, toluene and xylene; dimethyl sulfoxide and dimethylformamide.

If, in this reaction, a fatty acid salt is used as the carboxylic acid salt of formula (VII) and a fatty acid is used as the solvent, it is preferable to use, as the solvent, the fatty acid corresponding to said carboxylic acid salt of formula (VII). For example, when the carboxylic acid salt of formula (VII) is sodium acetate, the solvent is preferably acetic acid.

The carboxylic acid salt of formula (VII) is used usually in an amount of 1-10 moles, preferably 1.5-5 moles, per 1 mole of the compound of formula (VI).

The reaction temperature and the reaction time are selected from wide ranges in accordance with the kinds of starting material and solvent. It is usually preferable to carry out the reaction at temperature from room temperature (about 20° C.) to the boiling point of the solvent used in the reaction. The reaction is usually completed in about 10 hours.

The examples of $R_5$ in the formula (VII) are hydrogen atom, an alkyl such as methyl, ethyl, propyl, butyl, pentyl, hexyl and heptadecyl; an aryl such as phenyl and naphthalyl and an aralkyl such as benzyl, phenylethyl and naphthylmethyl. An alkyl is not only straight chain but also may be branched if it may be branched. Further, these alkyl, phenyl, naphthyl may be substituted with other substituents other than hydrogen unless they have an undesirable effect on the reaction.

The examples of M in the formula (VII) are alkali metals such as sodium and potassium and alkaline earth metals such as calcium and magnesium, provided that n is 1 when M is an alkali metal and n is 2 when M is an alkaline earth metal. It is sometimes preferable to carry out this reaction in the presence of a catalyst. Particularly when the above-mentioned ketones, cyclic ethers or aromatic hydrocarbons are used as the solvent, the reaction is preferably conducted in the presence of the catalyst such as a crown ether typified by 18-crown-6, among which 18-crown-6 itself is particularly preferable. It can be added in an amount of about 0.1–10% (by weight), preferably about 1–5% based on the carboxylic acid salt of formula (VII).

The subsequent step of hydrolysis can be practised in the same way as in the hydrolysis in the first step of (C).

Next, the second method of (b) wherein decarboxylation is carried out at the beginning which is followed by the reaction with the carboxylic acid salt of formula (VII) and hydrolysis will be illustrated.

The first decarboxylation from the compound of formula (VI) can be carried out by a mere heating in the presence or absence of a solvent. It is preferably carried out in a solvent inert to the reaction. Examples of the solvents are organic acids such as formic acid, acetic acid and propionic acid and aromatic hydrocarbons such as benzene, toluene, and xylene.

The reaction can be carried out at the temperature from 50° C. to 250° C. in general, the reaction is most preferably carried out at the temperature from 80° C. to 120° C. in the presence of the solvent. The reaction time varies depending on the temperature. The reaction usually can be completed in several minutes to about 3 hours.

By the decarboxylation, there is formed a compound represented by the following formula:

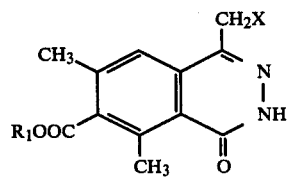

wherein $R_1$ and X are as defined above, as an intermediate. This intermediate may be isolated before reacting it with the carboxylic acid salt of formula (VII) in the subsequent step but the reaction mixture including said intermediate can also be used in the subsequent step. The reaction of said intermediate and the carboxylic acid salt of formula (VII) can be effected in the same way as in the above-mentioned reaction between the compound of formula (VI) and the carboxylic acid salt of formula (VII).

By the reaction between the compound of formula (XI) and the carboxylic acid salt of formula (VII), the above-mentioned compound of formula (X) is formed as an intermediate. Hydrolysis of this compound of formula (X) can be effected in the same manner as above.

Lastly, (c) of step (E) will be illustrated. When $R_4$ in formula (VI) is —CONH$_2$, the reaction of the compound of formula (VI) and the carboxylic acid salt of formula (VII) can be performed in the same way as the reaction in the method (b) of step (E).

Simultaneous hydrolysis and decarboxylation of the acyloxylated compound can be carried out in the same way as the hydrolysis used an acid in step (C).

The objective compound thus obtained i.e. 4-hydroxymethyl-1-phthalazone of formula (VIII) can be isolated by removing the organic solvent by a method such as distillation, followed by adjusting pH to about 4 and collecting the depositing crystals by filtration, when a solvent mixture comprising water and an organic solvent is used as the solvent.

This invention will be specified by the following Examples, which are presented in no limitative way.

EXAMPLE 1

Benzene (10 ml) is added to a mixture of 2.50 g of 3,5-dimethyl-4-ethoxycarbonylphthalic anhydride and 4.35 g of methoxycarbonylmethylenetriphenylphosphorane, and the mixture is reacted at room temperature with stirring for 4 hours. After the reaction, the solvent is distilled off under reduced pressure to give a crude product. It is subjected to a column chromatography using 150 g of silica gel and a benzene-ethyl acetate mixture as the developing solvent, whereby the two products having a relation of geometric isomer to each other can be isolated:

methyl (Z)-5,7-dimethyl-6-ethoxycarbonylphthalide-$\Delta^{3,\alpha}$-methylenecarboxylate; 2.20 g (yield 72.3%); m.p. 122.0°–122.5° C.

methyl (E)-5,7-dimethyl-6-ethoxycarbonylphthalide-$\Delta^{3,\alpha}$-methylenecarboxylate; 0.34 g (yield 11.2%); m.p. 134°–136° C.

EXAMPLE 2

Benzene (30 ml) is added to a mixture of 3.72 g of 3,5-dimethyl-4-ethoxycarbonylphthalic anhydride and 6.20 g of ethoxycarbonylmethylenetriphenylphosphorane and the mixture is reacted at room temperature for 3 hours with stirring. After the reaction the deposited crystals are collected by filtration, and there is obtained 1.23 g (yield 25.8%) of ethyl (Z)-5,7-dimethyl-6-ethoxycarbonylphthalide-$\Delta^{3,\alpha}$-methylenecarboxylate; m.p. 114°–114.5° C.

The filtrate is concentrated, and the residue is subjected to silica gel chromatography in the same manner as in Example 1, and there is additionally obtained 2.11 g (yield 44.2%) of ethyl (Z)-5,7-dimethyl-6-ethoxycarbonylphthalide-$\Delta^{3,\alpha}$-methylenecarboxylate. By this chromatography, there is simultaneously obtained 0.80 g (yield 16.8%) of ethyl (E)-5,7-dimethyl-6-ethoxycarbonylphthalide-$\Delta^{3,\alpha}$-methylenecarboxylate; m.p. 105°–108° C.

EXAMPLE 3

Benzene (3 ml) is added to a mixture of 0.50 g of 3,5-dimethyl-4-methoxycarbonylphthalic anhydride and 0.97 g of ethoxycarbonylmethylenetriphenylphosphorane, the mixture is reacted at room temperature for 3 hours with stirring and the deposited crystals are collected by filtration, whereby 0.26 g (yield 40.1%) of ethyl (Z)-5,7-dimethyl-6-methoxycarbonylphthalide-$\Delta^{3,\alpha}$-methylenecarboxylate is obtained; m.p. 127°–128.5° C.

EXAMPLE 4

Ethyl (Z)-5,7-dimethyl-6-ethoxycarbonylphthalide-$\Delta^{3,\alpha}$-methylenecarboxylate (2.48 g) is added into a mixture of 50 ml of n-propanol and 4.70 g of 80% aqueous solution of hydrazine hydrate, and then the mixture is heated under reflux at 110° C. for 10 hours. The reaction mixture is cooled and the deposited crystals are collected by filtration to obtain 2.25 g (yield 90.7%) of 6,8-dimethyl-7-ethoxycarbonyl-1-phthalazone-4-acetic acid hydrazide.

m.p. 243°–245° C. (decomposition with foaming)

IR spectrum: $\nu_{max}^{KBr}$ (cm$^{-1}$)=3320, 3180, 1724, 1655, 1604, 1526, 1280

NMR spectrum (DMSO-d$_6$): $\delta$=1.35 (t, 3H, J=7 Hz; OCH$_2$CH$_3$), 2.39, 2.78 (s, s, 3H, 3H; phenyl—CH$_3$), 3.72 (s, 2H; $\overline{\text{CH}}_2$), 4.40 (q, 2H, J=7 Hz); OCH$_2$CH$_3$), 3.5–4.7 (broad, 2H; NH$_2$), 7.60 (s, 1H; phenyl—$\overline{\text{H}}$), 9.25 (s, 1H; N$\overline{\text{H}}$NH$_2$), 12.36 (s, 1H; NH—N=)

EXAMPLE 5

Ethyl (E,Z)-5,7-dimethyl-6-ethoxycarbonylphthalide-$\Delta^{3,\alpha}$-methylenecarboxylate [the above-mentioned geometric isomer mixture, (III'):(III")=9:4] (0.33 g) is dissolved into 7 ml of n-propanol, to which is added 0.63 g of 80% aqueous solution of hydrazine hydrate. The reaction and the after-treatment are carried out in the same manner as in Example 4, whereby 0.31 g (yield 93.6%) of 6,8-dimethyl-7-ethoxycarbonyl-1-phthalazone-4-acetic acid hydrazide is obtained.

This product perfectly coincides with the product of Example 4 in m.p., IR and NMR spectra.

EXAMPLE 6

Ethyl (Z)-5,7-dimethyl-6-methoxycarbonylphthalide-$\Delta^{3,\alpha}$-methylenecarboxylate (0.20 g) is dissolved into 4 ml of n-propanol, to which is added 0.41 g of 80% aqueous solution of hydrazine hydrate. Thereafter, the reaction and the after-treatment are carried out in the same manner as in Example 4. Thus 0.14 g (yield 68.2%) of 6,8-dimethyl-7-methoxycarbonyl-1-phthalazone-4-acetic acid hydrazide is obtained.

m.p. 257.5°–259.0° C. (decomposition with foaming)

IR spectrum: $\theta_{max}^{KBr}$ (cm$^{-1}$)=3300, 3170, 3040, 2940, 1725, 1650, 1603, 1532, 1435, 1285

NMR spectrum (DMSO-d$_6$): $\delta$=2.38, 2.76 (s, s, 3H, 3H; phenyl—CH$_3$), 3.72 (s, 2H; CH$_2$), 3.94 (s, 3H; CH$_3$O), 3.6–4.7 (broad, 2H; NH$_2$), 7.64 (s, 1H; phenyl—H), 9.26 (s, 1H; N$\overline{\text{H}}$NH$_2$), 12.38 (s, 1H; NH—N=)

EXAMPLE 7

3,5-Dimethyl-4-ethoxycarbonylphthalic anhydride (25.0 g) and 43.5 g of methoxycarbonylmethylenetriphenylphosphorane are added to 100 ml of benzene and stirred at 20°–25° C. for 4 hours. After the reaction, the reaction mixture is concentrated under reduced pressure, the residue is added into 800 ml of n-propanol and 64.0 g of 80% aqueous solution of hydrazine hydrate is added, and the mixture is heated under reflux for 10 hours. The reaction mixture is cooled and the depositing crystals are collected by filtration. Thus, 27.2 g (yield 85.4%) of 6,8-dimethyl-7-ethoxycarbonyl-1-phthalazone-4-acetic acid hydrazide is obtained. This product perfectly coincides with the product of Example 4 in m.p., IR and NMR spectra.

EXAMPLE 8

6,8-Dimethyl-7-ethoxycarbonyl-1-phthalazone-4-acetic acid hydrazide (12.00 g) is added to 380 ml of 2N hydrochloric acid and heated under reflux for 5 hours. The reaction mixture is cooled and the depositing crystals are collected by filtration, washed with water and dried. Thus, 10.2 g (yield 89.0%) of 6,8-dimethyl-7-ethoxycarbonyl-1-phthalazone-4-acetic acid is obtained.

m.p. 162.5°–163.5° C. (decomposition with foaming)

IR spectrum: $\nu_{max}^{KBr}$ (cm$^{-1}$)=3240, 2300–3000 (broad), 1730, 1700 (shoulder), 1640, 1602, 1280

NMR spectrum (DMSO-d$_6$): $\delta$=1.37 (t, 3H, J=7 Hz; OCH$_2$CH$_3$), 2.42, 2.82 (s, s, 3H, 3H; phenyl—CH$_3$), 3.94 (s, 2H; $\overline{\text{CH}}_2$), 4.43 (q, 2H, J=7 Hz; OCH$_2$CH$_3$), 2–6 (broad, 1H; COOH), 7.61 (s, 1H; phenyl—$\overline{\text{H}}$), 12.45 (s, 1H; NH)

EXAMPLE 9

6,8-Dimethyl-7-ethoxycarbonyl-1-phthalazone-4-acetic acid anhydride (2.00 g) is added to 50 ml of 3N hydrochloric acid and heated under reflux for 2 hours, after which it is treated in the same manner as in Example 8. Thus, 1.80 g (yield 94.4%) of 6,8-dimethyl-7-methoxycarbonyl-1-phthalazone-4-acetic acid is obtained.

m.p. 203°–205° C. (decomposition with foaming)

IR spectrum: $\nu_{max}^{KBr}$ (cm$^{-1}$)=3300, 3160, 3035, 2300–3000 (broad), 1733, 1697, 1663, 1603, 1438, 1290, 1250, 1175, 1145

NMR spectrum (DMSO-d$_6$): $\delta$=2.40, 2.78 (s, s, 3H, 3H; phenyl—CH$_3$), 3.96 (s, 5H; CH$_2$, CH$_3$O), 5–10 (broad, 1H; COOH), 7.61 (s, 1H; phenyl—H), 2.45 (s, 1H; NH)

EXAMPLE 10

6,8-Dimethyl-7-ethoxycarbonyl-1-phthalazone-4-acetic acid (0.40 g) is dissolved into 10 ml of glacial acetic acid, 0.24 g of bromine is added thereto, and the mixture is reacted at room temperature for 3 hours with stirring. The acetic acid is distilled off under reduced pressure, water is added to the residue, the deposited crystals are collected by filtration and the crystals recrystallized from acetone-n-hexane mixture. Thus, 0.47 g (yield 92.9%) of 6,8-dimethyl-7-ethoxycarbonyl-1-phthalazone-4-$\alpha$-bromoacetic acid is obtained. m.p. 202.5°–204° C.

IR spectrum: $\nu_{max}^{KBr}$ (cm$^{-1}$)=3170, 2200–3000 (broad), 1730, 1660, 1605, 1278, 1240, 1145, 1120

NMR spectrum (DMSO-d$_6$): δ=1.40 (t, 3H, J=7 Hz; OCH$_2$CH$_3$), 2.45, 2.80 (s, s, 3H, 3H; phenyl—CH$_3$), 4.46 (q, 2H, $\overline{J}$=7 Hz; OCH$_2$CH$_3$), 4–7 (broad, 1H; COOH), 6.47 (s, 1H; CHBr), 7.87 (s, 1H; phenyl—H), 12.77 (s, 1H; NH)

EXAMPLE 11

6,8-Dimethyl-7-ethoxycarbonyl-1-phthalazone-4-acetic acid (1.00 g) is dissolved into 20 ml of glacial acetic acid, 0.61 g of sulfuryl chloride is added thereto, and the mixture is reacted at room temperature for 7 hours with stirring. The mixture is concentrated under reduced pressure and the residue is recrystallized from an acetone-n-hexane mixture. Thus, 1.00 g (yield 89.4%) of 6,8-dimethyl-7-ethoxycarbonyl-1-phthalazone-4-α-chloroacetic acid is obtained.

m.p. 188°–189° C.

IR spectrum: $\nu_{max}^{KBr}$ (cm$^{-1}$)=3026, 2200–3000 (broad), 1730, 1663, 1603, 1277, 1240, 1150, 1120

NMR spectrum (DMSO-d$_6$): δ=1.38 (t, 3H, J=7 Hz; OCH$_2$CH$_3$), 2.46, 2.82 (s, s, 3H, 3H; phenyl—CH$_3$), 4.45 (q, 2H, $\overline{J}$=7 Hz; OCH$_2$CH$_3$), 4–7 (broad, COOH), 6.40 (s, 1H; ClCH), 7.85 (s, 1H; phenyl—H), 12.77 (s, 1H; NH)

EXAMPLE 12

6,8-Dimethyl-7-methoxycarbonyl-1-phthalazone-4-acetic acid (1.27 g) is suspended in 40 ml of glacial acetic acid, 0.77 g of sulfuryl chloride is added thereto, the mixture is reacted at room temperature for 4 hours with stirring, and thereafter it is treated in the same manner as in Example 11. Thus, 1.10 g (yield 77.4%) of 6,8-dimethyl-7-methoxycarbonyl-1-phthalazone-4-α-chloroacetic acid is obtained.

m.p. 249°–250° C. (decomposition)

IR spectrum: $\nu_{max}^{KBr}$ (cm$^{-1}$)=3160, 3040, 2930, 2300–3000 (broad), 1730, 1667, 1603, 1440, 1283, 1242, 1145, 1118

NMR spectrum (DMSO-d$_6$): δ=2.42, 2.78 (s, s, 3H, 3H; phenyl—CH$_3$), 3.96 (s, 3H; CH$_3$O), 6.38 (s, 1H; CHCl), 7.83 (s, 1H; phenyl—H), 9.32 (broad, 1H; COOH), 12.75 (s, 1H; NH)

EXAMPLE 13

6,8-Dimethyl-7-ethoxycarbonyl-1-phthalazone-4-α-bromoacetic acid (3.80 g) is dissolved into 100 ml of glacial acetic acid and heated at 100° C. for 2 hours with stirring. The reaction mixture is concentrated under reduced pressure, water is added to the residue, and the resulted crystals are collected by filtration to obtain a crude product. It is recrystallized from benzene, and there is obtained 2.90 g (yield 85.5%) of ethyl 4-bromomethyl-6,8-dimethyl-1-phthalazone-7-carboxylate.

m.p. 202°–203° C.

EXAMPLE 14

6,8-Dimethyl-7-ethoxycarbonyl-1-phthalazone-4-α-chloroacetic acid (3.40 g) is dissolved into 100 ml of glacial acetic acid and the mixture is reacted and after-treated in the same manner as in Example 13. Thus, 2.65 g (yield 89.9%) of ethyl 4-chloromethyl-6,8-dimethyl-1-phthalazone-7-carbozylate is obtained.

m.p. 184°–186° C.

EXAMPLE 15

6,8-Dimethyl-7-ethoxycarbonyl-1-phthalazone-4-α-chloroacetic acid (0.50 g) is dissolved into 20 ml of toluene and reacted at 90° C. for 2 hours with stirring. The mixture is cooled and the deposited crystals are collected by filtration. Thus, 0.31 g (yield 70.1%) of ethyl 4-chloromethyl-6,8-dimethyl-1-phthalazone-7-carboxylate is obtained. It coincides with the product of Example 14 in melting point.

EXAMPLE 16

6,8-Dimethyl-7-methoxycarbonyl-1-phthalazone-4-α-chloroacetic acid (0.97 g) is dissolved into 30 ml of glacial acetic acid and reacted and after-treated in the same manner as in Example 13. Thus, 0.73 g (yield 86.7%) of methyl 4-chloromethyl-6,8-dimethyl-1-phthalazone-7-carboxylate is obtained.

m.p. 253°–255° C.

EXAMPLE 17

6,8-Dimethyl-7-ethoxycarbonyl-1-phthalazone-4-acetic acid (2.00 g) is dissolved into 50 ml of glacial acetic acid, to which is added 1.20 g of bromine. The mixture is reacted at room temperature for 3 hours and then heated at 100° C. for 2 hours. The reaction mixture is cooled, water is added thereto, the deposited crystals are collected by filtration, and the crystals are recrystallized from benzene. Thus, 1.80 g (yield 80.4%) of ethyl 4-bromomethyl-6,8-dimethyl-1-phthalazone-7-carboxylate is obtained. This product perfectly coincides with the product of Example 13 in melting point.

EXAMPLE 18

Ethyl 4-bromomethyl-6,8-dimethyl-1-phthalazone-7-carboxylate (3.40 g) is dissolved into 50 ml of dimethylformamide, 2.04 g of sodium formate is then added thereto, and the mixture is reacted at 60° C. for 1 hour with stirring. The reaction mixture is concentrated under reduced pressure to distil off the solvent, water is added to the residue, the resultant crystals are collected by filtration, and the crystals are recrystallized from ethanol. Thus, 2.42 g (yield 79.6%) of ethyl 6,8-dimethyl-4-formyloxymethyl-1-phthalazone-7-carboxylate is obtained.

m.p. 152°–154° C.

EXAMPLE 19

Ethyl 4-bromomethyl-6,8-dimethyl-1-phthalazone-7-carboxylate (15.00 g) is dissolved into 300 ml of glacial acetic acid, then 10.80 g of sodium acetate is added thereto, and the mixture is reacted under reflux with stirring and heating for 7 hours. The reaction mixture is treated in the same manner as in Example 18, and there is obtained 13.65 g (yield 97.0%) of ethyl 4-acetoxymethyl-6,8-dimethyl-1-phthalazone-7-carboxylate.

m.p. 162°–164° C.

EXAMPLE 20

Ethyl 4-bromomethyl-6,8-dimethyl-1-phthalazone-7-carboxylate (3.40 g) is dissolved into 40 ml of dimethylformamide, 2.89 g of sodium propionate is added thereto, and the mixture is reacted at 60° C. for 1 hour. The reaction mixture is concentrated under reduced pressure. The residue is dissolved into 200 ml of ethyl acetate, the solution washed with water and dehydrated and dried over magnesium sulfate. The magnesium sulfate is filtered off, the filtrate is concentrated under reduced pressure, and the residue is recrystallized from ethanol. Thus, 2.79 g (yield 84.7%) of ethyl, 6,8-dimethyl-4-propionyloxymethyl-1-phthalazone-7-carboxylate is obtained.

m.p. 130°–132° C.

EXAMPLE 21

Ethyl 4-chloromethyl-6,8-dimethyl-1-phthalazone-7-carboxylate (2.95 g) is dissolved into 110 ml of dimethylformamide, 9.20 g of sodium stearate is added thereto, and the mixture is reacted at 60° C. for 2 hours. The reaction mixture is concentrated under reduced pressure. The residue is dissolved into 500 ml of ethyl acetate, the solution thoroughly washed with warm water and then concentrated under reduced pressure to obtain a crude product. It is subjected to silica gel column chromatography by the use of a benzene-ethyl acetate solvent mixture, and there is obtained 3.61 g (yield 66.3%) of ethyl 6,8-dimethyl-4-stearoyloxymethyl-1-phthalazone-7-carboxylate.

m.p. 91°–93° C.

EXAMPLE 22

Ethyl 4-chloromethyl-6,8-dimethyl-1-phthalazone-7-carboxylate (2.95 g) is dissolved into 60 ml of tetrahydrofuran, then 2.88 g of sodium benzoate and 0.2 g of 18-crown-6 are added thereto, and the mixture is reacted at 50° C. for 2 hours. The reaction mixture is concentrated under reduced pressure to distil off the solvent, water is added to the residue, the precipitated crude crystals are collected by filtration, and then it is recrystallized from ethanol. Thus, 2.90 g (yield 76.2%) of ethyl 4-benzoyloxymethyl-6,8-dimethyl-1-phthalazone-7-carboxylate is obtained.

m.p. 178°–179° C.

EXAMPLE 23

Ethyl 4-chloromethyl-6,8-dimethyl-1-phthalazone-7-carboxylate (2.95 g) is dissolved into 60 ml of tetrahydrofuran, then 4.06 g of sodium p-nitrophenylacetate and 0.20 g of 18-crown-6 are added thereto, and thereafter the reaction and the after-treatments of the mixture are carried out in the same manner as in Example 22. The crude crystals are collected by filtration and recrystallized from a solvent mixture comprising ethanol and chloroform. Thus, 3.70 g (yield 84.3%) of ethyl 6,8-dimethyl-4-p-nitrophenylacetoxymethyl-1-phthalazone-7-carboxylate is obtained.

m.p. 222.5°–223° C. (decomposition with foaming)

EXAMPLE 24

Methy 4-chloromethyl-6,8-dimethyl-1-phthalazone-7-carboxylate (0.11 g) is dissolved into 3 ml of glacial acetic acid, then 0.32 g of sodium acetate is added thereto, and the mixture is reacted under reflux for 40 hours with stirring. The reaction mixture is treated in the same manner as in Example 18 to obtain a crude product. It is recrystallized from methanol, and there is obtained 0.10 g (yield 84.3%) of methyl 4-acetoxymethyl-6,8-dimethyl-1-phthalazone-7-carboxylate.

m.p. 185°–187° C.

EXAMPLE 25 n-Propyl 4-chloromethyl-6,8-dimethyl-1-phthalazone-7-carboxylate (0.31 g) is dissolved into 6.2 ml of glacial acetic acid, to which is added 0.49 g of sodium acetate. The mixture is reacted under reflux for 20 hours with stirring. The reaction mixture is treated in the same manner as in Example 18 and there is obtained 0.31 g (yield 93.9%) of n-propyl 4-acetoxymethyl-6,8-dimethyl-1-phthalazone-7-carboxylate.

m.p. 141°–142° C.

EXAMPLE 26

6,8-Dimethyl-7-ethoxycarbonyl-1-phthalazone-4-α-bromoacetic acid (3.83 g) is dissolved into 50 ml of formic acid, to which is added 3.40 g of sodium formate. With stirring, the mixture is reacted at 105° C. for 17 hours. After the reaction, the formic acid is distilled off under reduced pressure, water is added to the residue and the deposited crystals are collected by filtration. Thus, 2.85 g (yield 93.7%) of ethyl 6,8-dimethyl-4-formyloxymethyl-1-phthalazone-7-carboxylate is obtained.

This product perfectly coincides with the product of Example 18 in melting point.

EXAMPLE 27

6,8-Dimethyl-7-ethoxycarbonyl-1-phthalazone-4-α-bromoacetic acid (3.83 g) is dissolved into 70 ml of glacial acetic acid, to which is added 3.28 g of sodium acetate. The mixture is heated at 120° C. with stirring and reacted for 6 hours. After the reaction, the acetic acid is distilled off under reduced pressure, water is added to the residue, and the deposited crystals are collected by filtration. Thus, 3.14 g (yield 98.6%) of ethyl 4-acetoxymethyl-6,8-dimethyl-1-phthalazone-7-carboxylate is obtained.

This product perfectly coincides with the product of Example 19 in melting point.

EXAMPLE 28

6,8-Dimethyl-7-ethoxycarbonyl-1-phthalazone-4-α-chloroacetic acid (3.39 g) is dissolved into 70 ml of glacial acetic acid, to which is added 3.28 g of sodium acetate. Thereafter, the reaction and the after-treatment are carried out in the same manner as in Example 27. Thus, 3.10 g (yield 97.4%) of ethyl 4-acetoxymethyl-6,8-dimethyl-1-phthalazone-7-carboxylate is obtained. This product perfectly coincides with the product of Example 19 in melting point.

EXAMPLE 29

6.8-Dimethyl-7-methoxycarbonyl-1-phthalazone-4-α-chloroacetic acid (0.97 g) is dissolved into 20 ml of glacial acetic acid, to which is added 1.30 g of sodium acetate. Thereafter, the reaction and the after-treatment are carried out in the same manner as in Example 27. Thus, a crude product obtained is recrystallized from methanol to give 0.67 g (yield 73.4%) of methyl 4-acetoxymethyl-6,8-dimethyl-1-phthalazone-7-carboxylate.

m.p. 185°–187° C.

EXAMPLE 30

6,8-Dimethyl-7-ethoxycarbonyl-1-phthalazone-4-acetic acid (0.91 g) is dissolved into 20 ml of glacial acetic acid, to which is added 0.57 g of bromine. The mixture is reacted at room temperature for 3 hours with stirring, after which 0.99 g of sodium acetate is added and the resulted mixture is heated under reflux for 6 hours. The reaction mixture is concentrated under reduced pressure to distil off the solvent and the deposited crystals are collected by filtration. Thus, 0.94 g (yield 98.5%) of ethyl 4-acetoxymethyl-6,8-dimethyl-1-phthalazone-7-carboxylate is obtained. This product perfectly coincides with the product of Example 19 in melting point.

EXAMPLE 31

Ethyl 4-acetoxymethyl-6,8-dimethyl-1-phthalazone-7-carboxylate (6.40 g) is dissolved into a mixture of 60 ml of 1N sodium hydroxide solution and 60 ml of methanol and hydrolyzed at 20° C. for 3 hours with stirring. After the reaction the methanol is distilled off, and pH of this concentrated mixture is adjusted to 4 with 10% hydrochloric acid. The deposited crystals are collected by filtration and this crude crystals are recrystallized from aqueous ethanol. Thus 4.40 g (yield 79.6%) of ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

EXAMPLE 32

Ethyl 4-acetoxymethyl-6,8-dimethyl-1-phthalazone-7-carboxylate (3.18 g) is dissolved into a mixture comprising 30 ml of 1N hydrochloric acid and 30 ml of methanol and hydrolyzed at 60° C. for 5 hours with stirring. After the reaction, the methanol is distilled off, pH of the concentrated mixture is adjusted to 4 with 10% sodium hydroxide solution, and thereafter treated in the same manner as in Example 31. Thus, 2.10 g (yield 76.0%) of ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

EXAMPLE 33

Ethyl 6,8-dimethyl-4-formyloxymethyl-1-phthalazone-7-carboxylate (3.04 g) is dissolved into a mixture comprising 30 ml of 1N sodium hydroxide solution and 30 ml of methanol and hydrolyzed at 20° C. for one hour with stirring, after which it is treated in the same manner as in Example 31. Thus, 2.25 g (yield 81.4%) of ethyl 6,8-dimethyl-4-hydroxymethyl-1-phthalazone-7-carboxylate is obtained.

m.p. 171.5°–173° C.

This product perfectly coinicides with otherwise synthesized authentic sample in IR, NMR and UV spectra.

EXAMPLE 34

Ethyl 6,8-dimethyl-4-propionyloxymethyl-1-phthalazone-7-carboxylate (3.28 g) is dissolved into a mixture comprising 30 ml of 1N sodium hydroxide solution and 30 ml of methanol and hydrolyzed at 20° C. for one hour with stirring and then the reaction mixture is treated in the same manner as in Example 31. Thus, 2.14 g (yield 77.8%) of ethyl 6,8-dimethyl-4-hydroxymethyl-1-phthalazone-7-carboxylate is obtained.

m.p. 171°–173° C.

This product perfectly coincides with otherwise synthesized authentic sample in IR, NMR and UV spectra.

EXAMPLE 35

Ethyl 6,8-dimethyl-4-stearoyloxymethyl-1-phthalazone-7-carboxylate (2.17 g) is dissolved into a mixture comprising 30 ml 1N sodium hydroxide solution and 30 ml of methanol and hydrolyzed at 20° C. for 2 hours with stirring and then the reaction mixture is treated in the same manner as in Example 31. Thus, 0.81 g (yield 73.4%) of ethyl 6,8-dimethyl-4-hydroxymethyl-1-phthalazone-7-carboxylate is obtained.

m.p. 171°–173° C.

This product perfectly coincides with otherwise synthesized authentic sample in NMR, IR and UV spectra.

EXAMPLE 36

Ethyl 4-benzoyloxymethyl-6,8-dimethyl-1-phthalazone-7-carboxylate (1.90 g) is dissolved into a mixture comprising 20 ml of 1N sodium hydroxide solution and 20 ml of methanol and hydrolyzed at 20° C. for 5 hours with stirring and then the reaction mixture is treated in the same manner as in Example 31. Thus, 0.94 g (yield 68.0%) of ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

EXAMPLE 37

Ethyl 6,8-dimethyl-4-p-nitrophenylacetoxymethyl-1-phthalazone-7-carboxylate (2.20 g) is dissolved into a mixture comprising 20 ml of 1N sodium hydroxide solution and 20 ml of methanol and thereafter hydrolyzed and after-treated in the same manner as in Example 36. Thus, 0.86 g (yield 62.3%) of ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

EXAMPLE 38

Methyl 4-acetoxymethyl-6,8-dimethyl-1-phthalazone-7-carboxylate (0.31 g) is dissolved into a mixture comprising 10 ml of 1N sodium hydroxide solution and 10 ml of methanol and thereafter hydrolyzed and after-treated in the same manner as in Example 31. Thus, 0.20 g (yield 76.2%) of methyl 6,8-dimethyl-4-hydroxymethyl-1-phthalazone-7-carboxylate is obtained.

m.p. 202°–203° C.

This product perfectly coincides with otherwise synthesized authentic sample in IR, NMR and UV spectra.

EXAMPLE 39 n-Propyl 4-acetoxymethyl-6,8-dimethyl-1-phthalazone-7-carboxylate (1.66 g) is dissolved into a mixture comprising 20 ml of 1N sodium hydroxide solution and 20 ml of methanol and hydrolyzed at 20° C. for 2 hours with stirring and then the reaction mixture is treated in the same manner as in Example 31. Thus, 1.23 g (yield 84.7%) of n-propyl 6,8-dimethyl-4-hydroxymethyl-1-phthalazone-7-carboxylate is obtained.

m.p. 179°–180° C.

IR spectrum: $\nu_{max}^{KBr}$ (cm$^{-1}$)=3160, 2920, 1725, 1650, 1600, 1270, 1230, 1150, 1115, 1030

NMR spectrum (DMSO-d$_6$): δ=0.97 (t, 3H, J=7 Hz; OCH$_2$CH$_2$CH$_3$), 1.74 (multi, 2H; OCH$_2$CH$_2$CH$_3$), 2.40, 2.77 (s, s, 3H, 3H; phenyl—CH$_3$), 4.31 (t, 2H, J=7 Hz; OCH$_2$CH$_2$CH$_3$), 4.64 (d, 2H, J=6 Hz; CH$_2$OH), 5.4 (t, 1H, J=6 Hz; OH), 7,84 (s, 1H; phenyl—H), 12.36 (s, 1H; NH)

EXAMPLE 40

Ethyl 4-bromomethyl-6,8-dimethyl-1-pthalazone-7-carboxylate (1.70 g) is added to a mixture comprising 50 ml of water and 10 ml of dioxane, to which is added 1.30 g of sodium hydrogen carbonate. The mixture is heated under reflux for 10 hours to effect the hydrolysis. The reaction mixture is diluted with 150 ml of water, its pH is adjusted to 3 with 10% hydroclinic acid, the deposited crystals are collected by filtration, and the crystals are recrystallized from aqueous ethanol. Thus, 1.02 g (yield 74.0%) of ethyl 6,8-dimethyl-4-hydroxymethyl-1-phthalazone-7-carboxylate is obtained.

m.p. 171°–173° C.

This product perfectly coincides with otherwise synthesized authentic sample in IR, NMR and UV spectra.

EXAMPLE 41

Ethyl 4-chloromethyl-6,8-dimethyl-1-phthalazone-7-carboxylate (3.00 g) is added to a mixture comprising 100 ml of water and 10 ml of ethanol, to which is added 2.50 g of sodium hydrogen carbonate. The mixture is heated under reflux for 2 hours to effect the hydrolysis. After the reaction the mixture is concentrated to distil off the solvent and the condensed mixture is treated in the same manner as in Example 40. Thus, 2.20 g (yield 73.0%) of ethyl 6,8-dimethyl-4-hydroxymethyl-1-phthalazone-7-carboxylate is obtained.

m.p. 171°–173° C.

This product perfectly coincides with otherwise synthesized authentic sample in IR, NMR and UV spectra.

EXAMPLE 42

Ethyl 4-bromomethyl-6,8-dimethyl-1-phthalazone-7-carboxylate (1.00 g) is added to a mixture comprising 23 ml of dimethylformamide and 23 ml of water, to which is added 1.23 g of sodium acetate. The mixture is heated at 60° C. for 5 hours with stirring to effect the hydrolysis. After the reaction, the solvent is distilled off, water is added to the residue, its pH is adjusted to 4 with hydrochloric acid, the deposited crystals are collected by filtration and this crude product is recrystalllized from aqueous ethanol. Thus, 0.56 g (yield 68.8%) of ethyl 6,8-dimethyl-4-hydroxymethyl-1-phthalazone-7-carboxylate is obtained.

m.p. 171°–173° C.

This product perfectly coincides with otherwise synthesized authentic sample in IR, NMR and UV spectra.

EXAMPLE 43

Methyl 4-chloromethyl-6,8-dimethyl-1-phthalazone-7-carboxylate (0.56 g) is added to a mixture comprising 20 ml of water and 5 ml of ethanol, to which is added 0.50 g of sodium hydrogen carbonate. Thereafter, the mixture is reacted and after-treated in the same manner as in Example 41. Thus, 0.39 g (yield 74.3%) of methyl 6,8-dimethyl-4-hydroxymethyl-1-phthalazone-7-carboxylate is obtained.

m.p. 202°–203° C.

This product perfectly coincides with otherwise synthesized authentic sample in IR, NMR and UV spectra.

EXAMPLE 44 n-Propyl 4-chloromethyl-6,8-dimethyl-1-phthalazone-7-carboxylate (0.31 g) is added to a mixture comprising 10 ml of water and 2 ml of ethanol, to which is added 0.30 g of sodium hydrogen carbonate. Thereafter, the mixture is reacted and after-treated in the same manner as in Example 41. Thus, 0.20 g (yield 68.9%) of n-propyl 6,8-dimethyl-4-hydroxymethyl-1-phthalazone-7-carboxylate is obtained.

m.p. 179°–180° C.

This product perfectly coincides with the product of Example 39 in IR and NMR spectra.

EXAMPLE 45

6,8-Dimethyl-7-ethoxycarbonyl-1-phthalazone-4-α-chloroacetic acid (0.34 g) is added to a solution of 0.42 g of sodium hydrogen carbonate in 5 ml of water. The mixture is heated at 110° C. for 6 hours with stirring to effect the hydrolysis. After the reaction, pH of the reaction mixture is adjusted to 2 with 1N hydrochloric acid, the separated oil is extracted with ethyl acetate, the ethyl acetate layer is washed with water and dried over anhydrous magnesium sulfate and the ethyl acetate is distilled off by concentration under reduced pressure. Thus, 0.26 g (yield 81%) of 6,8-dimethyl-7-ethoxycarbonyl-1-phthalazone-4-α-hydroxyacetic acid is obtained.

m.p. 124°–128° C.

IR spectrum: $\nu_{max}^{KBr}$ (cm$^{-1}$)=3700-3000 (broad), 3321, 2996, 3000-2200, 1730, 1645, 1635, 1605, 1440, 1430, 1275, 1240

NMR spectrum (DMSO-d$_6$): δ=1.35 (t, 3H, J=7 Hz; OCH$_2$CH$_3$), 2.38, 2.78 (s, s, 3H, 3H, phenyl—CH$_3$), 4.42 (q, 2H, J=7 Hz; OCH$_2$CH$_3$), 5.33 (s, 1H; CH), 4–8 (broad, 2H, OH; COOH), 7.86 (s, 1H; phenyl—H), 12.25 (s, 1H; NH)

In this Example, the 0.34 g of 6,8-dimethyl-7-ethoxycarbonyl-1-phthalazone-4-α-chloroacetic acid is replaced with 0.38 g of 6,8-dimethyl-7-ethoxycarbonyl-1-phthalazone-4-α-bromoacetic acid, and there can similarly be obtained 0.20 g (yield 62%) of 6,8-dimethyl-7-ethoxycarbonyl-1-phthalazone-4-hydroxyacetic acid.

EXAMPLE 46

6,8-Dimethyl-7-ethoxycarbonyl-1-phthalazone-4-α-hydroxyacetic acid (0.32 g) is added to 1 ml of 0.1N hydrochloric acid, to which is added 5 ml of water. The mixture is heated at 105°–110° C. for 10 hours with stirring to effect the decarboxylation. After the reaction, pH of the reaction mixture is adjusted to 4 with 0.1N sodium hydroxide solution, the deposited crystals are collected by filtration to obtain a crude product and it is recrystallized from aqueous ethanol. Thus, 0.21 g (yield 76%) of the objective product i.e. ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

In the same manner, methyl 6,8-dimethyl-4-hydroxymethyl-1-phthalazone-7-carboxylate can be obtained from 6,8-dimethyl-7-methoxycarbonyl-1-phthalazone-4-α-hydroxyacetic acid.

m.p. 202°–203° C.

This product perfectly coincides with otherwise synthesized authentic sample in IR, NMR and UV spectra.

EXAMPLE 47

6,8-Dimethyl-7-ethoxycarbonyl-1-phthalazone-4-α-bromoacetic acid (0.50 g) is added to 20 ml of water and heated at 100° C. for 20 hours with stirring to effect the hydrolysis and the decarboxylation simultaneously. After the reaction, the deposited crystals are collected by filtration, and there is obtained 0.25 g (yield 69%) of the objective compound i.e. ethyl 6,8-dimethyl-4-hydroxymethyl-1-phthalazone-7-carboxylate.

m.p. 171.5°–173° C.

This product perfectly coincides with otherwise synthesized authentic sample in IR, NMR and UV spectra.

Similarly, methyl 6,8-dimethyl-4-hydroxymethyl-1-phthalazone-7-carboxylate can be obtained from 6,8-dimethyl-7-methoxycarbonyl-1-phthalazone-4-α-bromoacetic acid.

m.p. 202°–203° C.

This product perfectly coincides with otherwise synthesized product in IR, NMR and UV spectra.

EXAMPLE 48

6,8-Dimethyl-7-ethoxycarbonyl-1-phthalazone-4-α-bromoacetic acid (0.38 g) is added to a solution of 0.42 g of sodium hydrogen carbonate in 5 ml of water, after which the reaction and the after-treatment are carried out in the same manner as in Example 45. Thus, 0.20 g (yield 62%) of the objective compound i.e. 6,8-dimethyl-7-ethoxycarbonyl-1-phthalazone-4-α-hydroxyacetic acid is obtained.

m.p. 124°–128° C.

This product perfectly coincides with the product of Example 45 in IR and NMR spectra.

EXAMPLE 49

6,8-Dimethyl-7-ethoxycarbonyl-1-phthalazone-4-α-bromoacetic acid (0.50 g) is added to 20 ml of water and heated at 100° C. for 20 hours with stirring to effect the hydrolysis and the decarboxylation simultaneously. After the reaction, the deposited crystals are collected by filtration and there is obtained 0.25 g (yield 69%) of ethyl 6,8-dimethyl-4-hydroxymethyl-1-phthalazone-7-carboxylate.

m.p. 171.5°–173° C.

This product perfectly coincides with otherwise synthesized authentic sample in IR, NMR and UV spectra.

Similarly, methyl 6,8-dimethyl-4-hydroxymethyl-1-phthalazone-7-carboxylate can be obtained from 6,8-dimethyl-7-methoxycarbonyl-1-phthalazone-4-α-bromoacetic acid.

m.p. 202°–203° C.

This product perfectly coincides with otherwise synthesized product in IR, NMR and UV spectra.

EXAMPLE 50

6,8-Dimethyl-7-ethoxycarbonyl-1-phthalazone-4-α-hydroxyacetic acid (0.32 g) is added to a solution of 65 mg of concentrated sulfuric acid in 6 ml of water, after which the reaction and the after-treatment are carried out in the same manner as in Example 46. Thus, 0.17 g (yield 62%) of the objective compound i.e. ethyl 6,8-dimethyl-4-hydroxymethyl-1-phthalazone-7-carboxylate is obtained.

m.p. 171.5°–173° C.

This product perfectly coincides with otherwise synthesized authentic sample in IR, NMR and UV spectra.

EXAMPLE 51

6,8-Dimethyl-7-ethoxycarbonyl-1-phthalazone-4-α-hydroxyacetic acid (0.32 g) is added to 5 ml of water, to which is further added 0.04 g of p-toluenesulfonic acid. Thereafter, the reaction and the after-treatment are carried out in the same manner as in Example 46, and there is obtained 0.20 g (yield 72%) of the objective compound i.e. ethyl 6,8-dimethyl-4-hydroxymethyl-1-phthalazone-7-carboxylate.

m.p. 171.5°–173° C.

This product perfectly coincides with otherwise synthesized authentic sample in IR, NMR and UV spectra.

EXAMPLE 52

Toluene (10 ml) is added to 2.48 g (10.0 mmol) of 3,5-dimethyl-4-ethoxycarbonylphthalic anhydride and 3.62 g (12.0 mmol) of cyanomethylenetriphenylphosphorane, and the mixture is reacted at room temperature overnight with stirring. The reaction mixture is concentrated under reduced pressure, and the residue is subjected to silica gel column chromatography [Merck Silica Gel ®, 70–230 mesh, 150 g; developed with benzene-ethyl acetate (20:1 v/v)] to separate the two products having the relation of geometric isomer each other. The fractions containing respective isomers are collected and concentrated under reduced pressure to obtain the followings:

(Z)-3-cyanomethylene-5,7-dimethyl-6-ethoxycarbonylphthalide 433 mg (1.60 mmol), yield 16.0%, m.p. 108°–109° C.

(E)-3-cyanomethylene-5,7-dimethyl-6-ethoxycarbonylphthalide 329 mg (1.20 mmol), yield 12.0%, m.p. 135°–136° C.

EXAMPLE 53

(Z)-3-Cyanomethylene-5,7-dimethyl-6-ethoxycarbonylphthalide 0.10 g (0.37 mmol) is dissolved into 3.0 ml of ethanol, to which is added 0.23 g (3.7 mmol) of 80% aqueous solution of hydrazine hydrate. The mixture is heated under reflux overnight. The reaction mixture is concentrated under reduced pressure and the residue is recrystallized from ethanol. Thus, 0.65 g (0.23 mmol) of 4-cyanomethyl-6,8-dimethyl-7-ethoxycarbonyl-1-phthalazone is obtained. Yield 62%.

m.p. 191°–192° C.

IR spectrum: $\nu_{max}^{KBr}$ (cm$^{-1}$)=3160, 3050, 2950, 2260, 1730, 1650, 1605, 1278, 1247, 1153, 1122, 1040

NMR spectrum (CDCl$_3$): δ=1.37 (t, 3H, J=7.0 Hz; OCH$_2$CH$_2$), 2.45, 2.82 (s, s, 3H, 3H; phenyl-CH$_3$), 4.43 (s, 2H; —CH$_2$CN), 4.46 (q, 2H, J=7.0 Hz; OCH$_2$CH$_3$), 7.68 (s, 1H; phenyl-H), 12.15 (broad, 1H; NH).

EXAMPLE 54

Toluene (100 ml) is added to 12.40 g (50.0 mmol) of 3,5-dimethyl-4-ethoxycarbonylphthalic anhydride and 22.08 g (73.3 mmol) of cyanomethylenetriphenylphosphorane, and the mixture is reacted at room temperature overnight with stirring. The reaction mixture is concentrated under reduced pressure, the residue is dissolved into 250 ml of ethanol, 31.3 g (500 mmol) of 80% aqueous solution of hydrazine hydrate is added thereto, and the resulting mixture is heated under reflux overnight. After the reaction, the reaction mixture is concentrated under reduced pressure and the residue is separated and purified by silica gel column chromatography [Merck Silica Gel ®, 70–230 mesh, 1.2 kg; developed with toluene-ethyl acetate (3:1 v/v)]. Thus, 4.48 g (15.7 mmol) of ethyl 4-cyanomethyl-6,8-dimethyl-1-phthalazone-7-carboxylate is obtained. Yield 31.4%.

m.p. 191°-192° C.

This product well coincides with the product of Example 53 in IR and NMR spectra.

EXAMPLE 55

Ethyl 4-cyanomethyl-6,8-dimethyl-1-phthalazone-7-carboxylate (285 mg, 1.00 mmol) is dissolved into a solvent mixture comprising 2 ml of glacial acetic acid and 1 ml of acetic anhydride, to which is added 0.70 g (4.4 mmol) of bromine. The mixture is reacted at room temperature overnight with stirring. The reaction mixture is diluted with 50 ml of chloroform and washed with cold water. The chloroform layer is dried over with anhydrous sodium sulfate and then concentrated under reduced pressure. The residue is recrystallized from 10 ml of benzene, and there is obtained 278 mg (0.76 mmol) of ethyl 4-bromocyanomethyl-6,8-dimethyl-1-phthalazone-7-carboxylate. Yield 76%.

m.p. 197°-199° C.

EXAMPLE 56

Ethyl 4-cyanomethyl-6,8-dimethyl-1-phthalazone-7-carboxylate (0.57 g, 2.0 mmol) is dissolved into 6 ml of glacial acetic acid, to which is added 0.40 g (2.5 mmol) of bromine. The mixture is reacted at room temperature overnight with stirring. After the reaction, 0.36 g of 95% sulfuric acid added to the reaction mixture and heated at 80° C. for one hour. After heating, the reaction mixture is cooled to room temperature, concentrated under reduced pressure, the residue is disolved in 200 ml of chloroform and then the solution is washed with water. The organic layer is dried over with anhydrous sodium sulfate and concentrated under reduced pressure, and the residue is recrystallized from 20 ml of chloroform. Thus, 0.65 g (1.7 mmol) of ethyl 4-(α-bromo-α-carbamoylmethyl)-6,8-dimethyl-1-phthalazone-7-carboxylate is obtained. Yield 85%.

m.p. 209°-211° C. (decomposition)

IR spectrum: $\nu_{max}^{KBr}$ (cm$^{-1}$)=3400, 3200, 3000, 2950, 1720, 1660, 1600, 1300, 1280, 1240, 1140, 1120, 1040.

NMR spectrum (DMSO-d$_6$): δ=1.33 (t, 3H, J=7.0 Hz; OCH$_2$CH$_3$, 2.39, 2.76 (s, s, 3H, 3H; phenyl-CH$_3$), 4.40 (q, 2H, J=7.0 Hz; OCH$_2$CH$_3$), 6.12 (s, 1H; CHBr), 7.63 (s, 2H; CONH$_2$), 7.82 (s, 1H; phenyl-H), 12.70 (s, 1H; NH).

EXAMPLE 57

Ethyl 4-(α-bromo-α-carbamoylmethyl)-6,8-dimethyl-1-phthalazone-7-carboxylate (3.82 g, 10 mmol) is dissolved into 38 ml of n-propanol, to which is added 19 ml of concentrated hydrochloric acid. The mixture is heated under reflux for 24 hours. The reaction mixture is concentrated under reduced pressure to distil off the solvent and 5.0 ml of distilled water is added to the residue. The deposited crystals are collected by filtration, washed with water and dried to obtain 0.83 g (30 mmol) of ethyl 6.8-dimethyl-4-hydroxymethyl-1-phthalazone-7-carboxylate. Yield 30%.

A portion of the crystals obtained herein is recrystallized from aqueous ethanol. It well coincides with authentic sample in NMR, IR and UV spectra.

EXAMPLE 58

Ethyl 4-cyanomethyl-6,8-dimethyl-1-phthalazone-7-carboxylate (285 mg 10 mmol) is dissolved into 1 ml of 95% sulfuric acid with cooling and stirred at room temperature for 5 hours to complete the reaction. The reaction mixture is poured into crushed ice and the resulted precipitates are collected by filtration. It is recrystallized from aqueous ethanol, and there is obtained 269 mg (0.887 mmol) of ethyl 4-carbamoylmethyl-6,8-dimethyl-1-phthalazone-7-carboxylate. Yield 88.7%.

m.p. 248°-258° C.

IR spectrum: $\nu_{max}^{KBr}$ (cm$^{-1}$)=3420, 3300, 3180, 2950, 1730, 1670, 1653, 1620, 1603, 1280, 1250, 1200, 1150, 1125, 1038.

NMR spectrum (DMSO-d$_6$): δ=1.33 (t, 3H, J=7.0 Hz; OCH$_2$CH$_3$), 2.38, 2.77 (s, s, 3H, 3H; phenyl-CH$_3$), 3.75 (s, 2H; CH$_2$CONH$_2$), 4.42 (q, 2H, J=7.0 Hz; OCH$_2$CH$_3$), 7.05 (s, 1H, the other H of CH$_2$CONH$_2$), 7.58 (s, 2H, the other H of CH$_2$CONH$_2$ and phenyl-H), 12.36 (s, 1H, NH).

EXAMPLE 59

Glacial acetic acid (4 ml) is added to 121 mg (0.40 mmol) of ethyl 4-carbamoylmethyl-6,8-dimethyl-1-phthalazone-7-carboxylate, to which is added 67 mg (0.42 mmol) of bromine. The mixture is reacted at room temperature overnight with stirring. The reaction mixture is concentrated under reduced pressure, the residue is disolved in 50 ml of chloroform and washed with water. The organic layer is dried over with anhydrous sodium sulfate and then concentrated under reduced pressure, and the residue is recrystallized from 5 ml of chloroform. Thus, 130 mg (0.34 mmol) of ethyl 4-(α-bromo-α-carbamoylmethyl)-6,8-dimethyl-1-phthalazone-7-carboxylate is obtained. Yield 85%.

m.p. 209°-211° C. (decomposition)

This product well coincides with the product of Example 56 in IR and NMR spectra.

EXAMPLE 60

Ethyl 4-cyanomethyl-6,8-dimethyl-1-phthalazone-7-carboxylate (285 mg, 1.00 mmol) is added to a mixture comprising 2.0 ml of concentrated hydrochloric acid and 2.0 ml of dioxane and heated under reflux overnight to complete the reaction. The reaction mixture is concentrated under reduced pressure, water is added to the residue, and the deposited crystals are collected by filtration, washed with water and recrystallized from aqueous acetone. Thus, 260 mg (0.856 mmol) of 6.8-dimethyl-7-ethoxycarbonyl-1-phthalazone-7-acetic acid is obtained. Yield 85.6%.

m.p. 162°-163° C. (decomposition with foaming)

This product perfectly coincides with the product of Example 8 in IR and NMR spectra.

EXAMPLE 61

Ethyl 4-carbamoylmethyl-6,8-dimethyl-1-phthalazone-7-carboxylate (303 mg, 1.00 mmol) is added to 5.0 ml of 2N hydrochloric acid and reacted for 5 hours while heating it under reflux. After the reaction, the reaction mixture is cooled and the deposited crystals are collected by filtration, washed with water and dried. Thus, 274 mg (0.901 mmol) of 6.8-dimethyl-7-ethoxycarbonyl-1-phthalazone-4-acetic acid is obtained. Yield 90.1%.

m.p. 162.5°-163.5° C. (decomposition with foaming)

This product well coincides with the product of Example 8 in IR and NMR spectra.

EXAMPLE 62

Ethyl 4-cyanomethyl-6,8-dimethyl-1-phthalazone-7-carboxylate (285 mg, 1.00 mmol) is added to a mixture comprising 6.0 ml of 2N aqueous solution of sodium hydroxide and 3.0 ml of n-propanol and the mixture is reacted overnight under reflux. The reaction mixture is concentrated under reduced pressure to distill off the solvent, water is added to the residue, pH of the aqueous mixture is adjusted to 1–2 with hydrochloric acid and the deposited crystals are collected by filtration, washed with water and recrystallized from aqueous acetone. Thus, 223 mg (0.733 mmol) of 6,8-dimethyl-7-ethoxycarbonyl-1-phthalazone-4-acetic acid is obtained. Yield 73.3%.

m.p. 163°–164° C. (decomposition with foaming)

This product well coincides with the product of Example 8 in IR and NMR spectra.

EXAMPLE 63

Ethyl 4-carbamoylmethyl-6,8-dimethyl-1-phthalazone-7-carboxylate (303 mg, 1.00 mmol) is added to a mixture comprising 6.0 ml of 2N aqueous solution of sodium hydroxide and 3.0 ml of ethanol and heated under reflux overnight. The reaction mixture is concentrated under reduced pressure to distil off the solvent, water is added to the residue, pH of the aqueous mixture is adjusted to 1–2 with hydrochloric acid, the deposited crystals are collected by filtration and the crystals are recrystallized from aqueous acetone. Thus, 211 mg (0.695 mmol) of 6,8-dimethyl-7-ethoxycarbonyl-1-phthalazone-4-acetic acid is obtained. Yield 69.5%. m.p. 163°–164° C. (decomposition with foaming).

This product well coincides with the product of Example 8 in IR and NMR spectra.

EXAMPLE 64

Ethyl 4-(α-bromo-α-carbamoylmethyl)-6,8-dimethyl-1-phthalazone-7-carboxylate (535 mg) is dissolved in 10 ml of glacial acetic acid. Then 574 mg of anhydrous sodium acetate is added to the solution. The mixture is reacted for 12 hours under reflux. After the reaction, the reaction mixture is concentrated under reduced pressure to distill off the solvent. Water is added to the residue and the deposited crystals are collected by filtration, washed with water and dried. Thus, 435 mg (yield 85.7%) of ethyl 4-(α-acetoxy-α-carbamoylmethyl)-6,8-dimethyl-1-phthalazone-7-carboxylate is obtained.

m.p. 210°–212° C.

EXAMPLE 65

Ethyl 4-(α-acetoxy-α-carbamoylmethyl)-6,8-dimethyl-1-phthalazone-7-carboxylate (0.72 g) is dissolved into 10 ml of n-propanol, to which 5 ml of concentrated hydrochloric acid is added. The mixture is reacted for 19 hours under reflux. The reaction mixture is concentrated under reduced pressure to distill off the solvent. The residue is diluted with 2 ml of water and the deposited crystals are collected by filtration, washed with water and dried. Thus, 0.43 g (yield 69%) of ethyl 6,8-dimethyl-4-hydroxymethyl-1-phthalazone-7-carboxylate is obtained.

m.p. 173°–175° C.

This product well coincides with otherwise synthesized product in IR, NMR and UV spectra.

What is claimed is:

1. 7-alkoxycarbonyl-6, 8-dimethyl-1-phthalazone-4-α-hydroxyacetic acid represented by the following formula

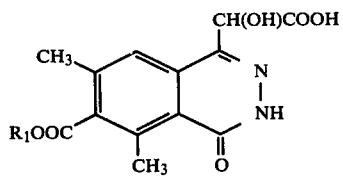

wherein $R_1$ is a lower alkyl, or a salt thereof.

2. The compound of claim 1 wherein $R_1$ is —$C_2H_5$.